(12) United States Patent
Okuda

(10) Patent No.: US 11,413,166 B2
(45) Date of Patent: Aug. 16, 2022

(54) PROSTHETIC LEG KNEE JOINT, BRAKING DEVICE, AND LOAD POSITION DETECTOR

(71) Applicant: NABTESCO CORPORATION, Tokyo (JP)

(72) Inventor: Masahiko Okuda, Tokyo (JP)

(73) Assignee: NABTESCO CORPORATION, Tokyo (JP)

( * ) Notice: Subject to any disclaimer, the term of this patent is extended or adjusted under 35 U.S.C. 154(b) by 30 days.

(21) Appl. No.: 16/725,091

(22) Filed: Dec. 23, 2019

(65) Prior Publication Data

US 2020/0397598 A1 Dec. 24, 2020

(30) Foreign Application Priority Data

Jun. 20, 2019 (JP) .............................. JP2019-114864

(51) Int. Cl.
| | |
|---|---|
| *A61F 2/64* | (2006.01) |
| *A61F 2/60* | (2006.01) |
| A61F 2/30 | (2006.01) |
| A61F 2/68 | (2006.01) |

(52) U.S. Cl.
CPC ................ *A61F 2/64* (2013.01); *A61F 2/604* (2013.01); *A61F 2/644* (2013.01); *A61F 2002/30329* (2013.01); *A61F 2002/6818* (2013.01); *A61F 2002/6827* (2013.01)

(58) Field of Classification Search
CPC .................................................... A61F 2/644
See application file for complete search history.

(56) References Cited

U.S. PATENT DOCUMENTS

| | | | | |
|---|---|---|---|---|
| 5,181,931 A | * | 1/1993 | van de Veen ........... | A61F 2/644 623/40 |
| 5,314,498 A | * | 5/1994 | Gramnas ................ | A61F 2/644 623/39 |
| 6,808,540 B1 | * | 10/2004 | Gramnas ................ | A61F 2/644 623/44 |

(Continued)

FOREIGN PATENT DOCUMENTS

| | | |
|---|---|---|
| GB | 2338653 A | 12/1999 |
| JP | H05237143 A | 9/1993 |

(Continued)

OTHER PUBLICATIONS

EPO Extended European Search Report for EP Application No. 19219515.4, dated Oct. 16, 2020.

(Continued)

*Primary Examiner* — Jacqueline Wozniki
(74) *Attorney, Agent, or Firm* — Cantor Colburn LLP

(57) ABSTRACT

A prosthetic leg knee joint includes a thigh connection part that is provided on the thigh side, a lower leg part that is provided rotatably around a knee shaft connected to the thigh connection part, a four-bar link mechanism that sets an instant center S whose relative position with respect to the thigh connection part is substantially constant regardless of the relative position between the thigh connection part and the lower leg part, and a braking unit that brakes the movement of the lower leg part in accordance with the relative position between the instance center S set by the four-bar link mechanism and the lower leg part.

8 Claims, 12 Drawing Sheets

(56) References Cited

U.S. PATENT DOCUMENTS

| | | | | |
|---|---|---|---|---|
| 2002/0026246 A1* | 2/2002 | Suzuki | ............ | A61F 2/644 |
| | | | | 623/46 |
| 2005/0203639 A1* | 9/2005 | Wild | ............ | A61F 2/644 |
| | | | | 623/44 |
| 2005/0234562 A1* | 10/2005 | Okuda | ............ | A61F 2/644 |
| | | | | 623/44 |
| 2007/0208430 A1* | 9/2007 | Gramnas | ............ | A61F 2/70 |
| | | | | 623/39 |
| 2014/0039642 A1* | 2/2014 | Nijiman | ............ | A61F 2/66 |
| | | | | 623/33 |
| 2014/0188252 A1* | 7/2014 | Sadler | ............ | A61F 2/644 |
| | | | | 623/46 |
| 2019/0262144 A1* | 8/2019 | Okuda | ............ | A61F 2/644 |

FOREIGN PATENT DOCUMENTS

| | | |
|---|---|---|
| JP | 2968597 B2 | 8/1999 |
| JP | 2000107212 A | 4/2000 |
| JP | 2004167106 A | 6/2004 |
| WO | 2005093305 A1 | 10/2005 |

OTHER PUBLICATIONS

Partial European Search Report issued for corresponding EP Patent Application No. 19219515.4; dated Jul. 15, 2020.
Katsumura et al., "Multiple Linkage Type Robotic Prosthesis to Prevent Trip and Fall", (2018 7th IEEE International Conference on Biomedical Robotics and Biomechatronics); 6 pages, dated (Aug. 36-29, 2018).

* cited by examiner

<Prior Art>

PROSTHETIC LEG KNEE JOINT, BRAKING DEVICE, AND LOAD POSITION DETECTOR

CROSS REFERENCE TO RELATED APPLICATIONS

The present application claims priority under 35 U.S.C. § 119 to Japanese Patent Application 2019-114864, filed on Jun. 20, 2019, the entire contents of which being incorporated herein by reference.

BACKGROUND OF THE INVENTION

1. Field of the Invention

The present invention relates to prosthetic leg knee joints.

2. Description of the Related Art

A function that allows for safe walking with high stability in the standing position (stance phase) is necessary for prosthetic leg knee joints. Conventionally, a technology for stabilizing a stance phase by a load brake that works according to the weight of a prosthetic leg wearer is known. Patent Document 1 discloses a load brake for use in a prosthetic leg that is provided with an upper member including a knee plate to which the load of a wearer is applied, a lower member to which a foot part is attached, and a knee shaft that is supported by the lower member and connects the upper member and the lower member swingably. The load brake includes a brake block connected to the knee plate by a pin. The brake block has a through-hole into which the knee shaft is inserted. When the load of the wearer is applied via the knee plate, the diameter of the through-hole decreases, tightening the knee shaft, and the rotation of the knee shaft is stopped.

In the load brake disclosed in Patent Document 1, in order to prevent a situation where the brake becomes effective during a push-off period in the latter half of a stance phase preventing a smooth shift to a swing phase, a pin for connecting the brake block to the knee plate is arranged near a load line in a swing transition period. However, when transitioning to the swing phase while applying a load to the back side such as when going down a hill, the load line moves backward from the knee shaft causing a load of a certain level or more to remain, and this sometimes causes the brake to work, which is so-called "trip". The load brake is provided with a coil spring. By adjusting the compression state of the coil spring, the effectiveness of the brake can be adjusted. This function has been used to make adjustments for preventing "trip" by lowering the braking force at the time of the transition to the swing phase. However, since the braking force in the stance phase is also lowered at the same time, there still remains a problem where a delicate adjustment is required. Since the way of walking differs depending on the person wearing the prosthetic leg and on the scene, there are times when it is not possible to eliminate "trip".

In the prosthetic leg disclosed in Patent Document 2, the above-described problem is solved by using a four-bar link mechanism. In this prosthetic leg, a rotary hydraulic braking circuit is used as a braking portion. The housing of the hydraulic braking circuit and the frame corresponding to a human shin are connected via a front link and a rear link. When it is assumed that the housing of the hydraulic braking circuit represents an upper link and the frame represents a lower link, a four-bar link mechanism is formed. An actuator of a switching valve of the hydraulic braking circuit is provided above the connecting part of the front link with the upper link, and the switching valve is operated by a force generated by a small rotational movement of the front link. The knee shaft, which defines the rotation axis of the knee flexion, coincides with the rotation axis of the hydraulic braking circuit and is connected to a lower leg part composed of a frame, a foot, and the connecting parts thereof. When the lower leg part rotates largely due to knee flexion, the hydraulic braking circuit and the switching valve rotate along with the lower leg part. In this prosthetic leg, the instant center of the four-bar link mechanism is placed between the toes of the foot part and the heel. When the weight is applied to the heel side, the load line (floor reaction force) is located behind the instant center, and the switching valve is thus closed due to deformation of the four-bar link mechanism, causing the brake to be applied to the prosthetic leg by the hydraulic braking circuit. On the other hand, when the weight is applied to the toe side, the load line is located in front of the instant center of rotation, and the switching valve thus becomes open due to deformation of the four-bar link mechanism, causing the brake on the prosthetic leg by the hydraulic braking circuit to be released. As described above, in the prosthetic leg disclosed in Patent Document 2, the instant center of the four-bar link mechanism is used as a sensing point to detect which part of the foot part the load of the prosthetic leg wearer is applied, and the hydraulic braking circuit can be controlled based on the detection result. Thus, a smooth transition to the swing phase is possible. In addition, since sufficient brake application force can be obtained even for adjustment using a spring, the stability during the stance phase has been dramatically increased.

On the other hand, when going down a steep hill, it is necessary to be able to support the weight during a toe strike state. Therefore, Patent Document 3 proposes that a mechanism that maintains the closed state of a hydraulic pressure switching valve be mounted on a prosthetic leg using the hydraulic pressure generated at the time of heel contact.

[Patent Document 1] Japanese Patent Application Publication No. 2000-107212

[Patent Document 2] Japanese Patent Application Publication No. 2004-167106

[Patent Document 3] International Publication No. 2005/93305

However, in the above prior art, when there is no heel contact before toe strike, no hydraulic pressure is generated since a switching valve remains open, and the weight may not be able to be supported. For example, such a situation can occur, e.g., when the toes of the foot part come in contact with the ground during swinging of the prosthetic leg in a swing phase or when the extension of an amputated end of the thigh is forgotten and a load is applied to the toe side at the time of stationary standing. In such a case, the weight cannot be supported by the residual muscular strength, and there is a possibility of causing unintentional knee flexion (i.e., knee bending).

SUMMARY OF THE INVENTION

In this background, a purpose of the present invention is to improve stability at the time of toe strike in a prosthetic leg knee joint that uses a link mechanism.

A prosthetic leg knee joint according to one embodiment of the present invention includes a thigh connection part that is provided on the thigh side, a lower leg part that is provided rotatably around a knee shaft connected to the thigh connection part, a reference position setting unit that sets a reference position whose relative position with respect to the thigh connection part is substantially constant, regardless of the relative position between the thigh connection part and the lower leg part, and a braking unit that brakes the movement of the lower leg part in accordance with the relative position between the reference position set by the reference position setting unit and the lower leg part.

Yet another embodiment of the present invention also relates to a prosthetic leg knee joint. This prosthetic leg knee joint includes: a thigh connection part that is provided on the thigh side; a lower leg part that is provided rotatably around a knee shaft connected to the thigh connection part; a multi-bar link mechanism that sets an instant center, whose relative position with respect to the thigh connection part is substantially constant regardless of the relative position between the thigh connection part and the lower leg part, between the vicinity of the sole and the vicinity of the hip joint of the prosthetic leg wearer; and a braking unit that brakes the movement of the lower leg part when the relative position between the instant center that has been set by the multi-bar link mechanism and the lower leg part is in a predetermined state due to the deformation of the multi-bar link mechanism. The multi-bar link mechanism consists of an upper link part provided in the thigh connection part, a lower link part provided in the braking unit, a front link part connecting a part of the upper link part and a part of the lower link part, and a rear link part connecting another part of the upper link part and another part of the lower link part. The length of the lower link part is shorter than the length of the upper link part.

Another embodiment of the present invention relates to a braking device. This device includes: a reference position setting unit that sets a reference position whose relative position with respect to a thigh connection part provided on the thigh side is substantially constant, regardless of the relative position between the thigh connection part and a lower leg part provided rotatably around a knee shaft connected to the thigh connection part; and a braking unit that brakes the movement of the lower leg part in accordance with the relative position between the reference position set by the reference position setting unit and the lower leg part.

Still another embodiment of the present invention relates to a load position detector. This detector includes: a reference position setting unit that sets a reference position whose relative position with respect to a thigh connection part that is provided on the thigh side is substantially constant, regardless of the relative positions of the thigh connection part and a lower leg part that is rotatable around a knee shaft connected to the thigh connection part; and a detection unit that detects the relative position between the reference position set by the reference position setting unit and the lower leg part.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

The invention will now be described by reference to the preferred embodiments. This does not intend to limit the scope of the present invention, but to exemplify the invention.

In the following embodiments, like numerals represent like constituting elements, and duplicative explanations will be omitted. For the sake of ease of explanation, some constituting elements are appropriately omitted in the figures.

An outline will be explained before specifically explaining a prosthetic leg knee joint according to an embodiment of the present invention. This prosthetic leg knee joint includes a thigh connection part that is provided on the thigh side of a prosthetic leg wearer, a lower leg part that is provided rotatably around a knee shaft connected to the thigh connection part, a reference position setting unit that sets a reference position whose relative position with respect to the thigh connection part is substantially constant within a finite distance from the knee shaft, regardless of the relative position between the thigh connection part and the lower leg part, and a braking unit that brakes the movement of the lower leg part in accordance with the relative position between the reference position set by the reference position setting unit and the lower leg part. The reference position is preferably set between the vicinity of the sole and the vicinity of the hip joint of the prosthetic leg wearer. In this aspect, the position where the load of the prosthetic leg wearer is applied is detected using the reference position as a sensing point, and the braking unit is controlled based on the detection result. In this aspect, the relative position between the reference position and the thigh connection part is substantially constant within a finite distance from the knee shaft, regardless of the relative position between the thigh connection part and the lower leg part. In other words, since the reference position hardly moves not only when the knee is extended but also when the knee is flexed, a wide stable operating range of the braking unit can be secured.

Thereby, even when a load is applied rearward from the toe or when a load is applied in the vertical direction from the toe, a braking force can be generated, and stability at the time of toe strike can be improved.

Figure 1:
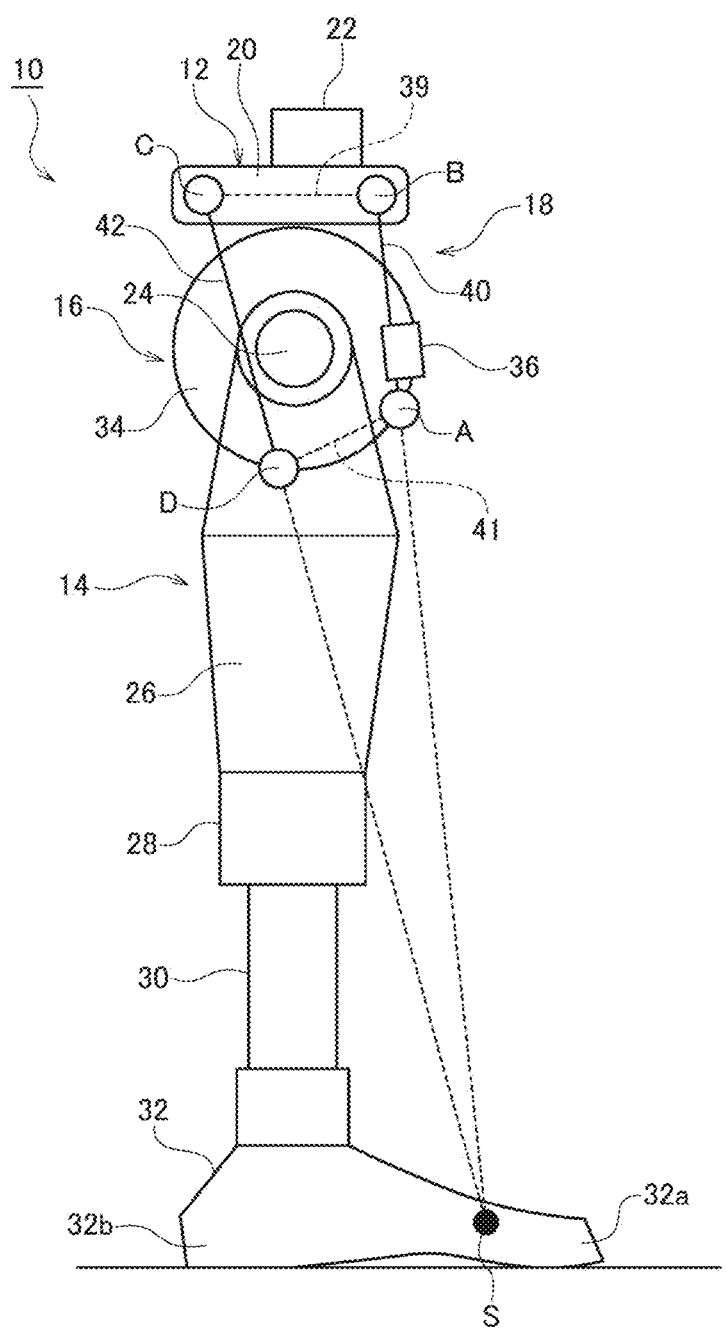
FIG. 1 is a diagram for explaining a prosthetic leg knee joint according to an embodiment of the present invention.

FIG. 1 is a diagram for explaining a prosthetic leg knee joint 10 according to an embodiment of the present invention. As shown in FIG. 1, the prosthetic leg knee joint 10 includes a thigh connection part 12, a lower leg part 14, a braking unit 16, and a four-bar link mechanism 18. In the prosthetic leg knee joint 10 according to the present embodiment, the four-bar link mechanism 18 serves as a reference position setting unit, and an instant center S that is set by the four-bar link mechanism 18 serves as a reference position. The braking unit 16 brakes the movement of the lower leg part 14 when the relative position between the instant center S and the lower leg part 14 is in a predetermined state due to the deformation of the four-bar link mechanism 18.

The thigh connection part 12 is located on the upper side of the knee and is connected to the thigh of the prosthetic leg wearer. The thigh connection part 12 includes a knee plate 20 made of, for example, an aluminum alloy and an alignment block 22 provided on the knee plate 20. The alignment block 22 is made of, for example, a titanium alloy, supports a socket (not shown), and supports the load of the prosthetic leg wearer through the thigh that goes into the socket.

The lower leg part 14 is located below the knee and is connected to the thigh connection part 12 via a knee shaft 24. The lower leg part 14 can rotate around the knee shaft 24 with respect to the thigh connection part 12. Due to the rotation around the knee shaft 24, the relative position between the thigh connection part 12 and the lower leg part 14 changes. The lower leg part 14 can rotate largely by, for example, 150° to 160° with respect to the thigh connection part 12. The prosthetic leg knee joint 10 according to the present embodiment is a single-shaft prosthetic leg knee joint with a single knee shaft 24. The lower leg part 14 includes a hollow frame 26 made of, for example, carbon fiber reinforced plastic, and a tightening member 28 provided at a lower part of the frame 26. The tightening member 28 is a member for connecting a leg pipe 30 to the frame 26. A foot part 32 is provided at the lower end of the leg pipe 30.

The braking unit 16 generates a braking force with respect to the rotational movement of the lower leg part 14 around the knee shaft 24 (that is, with respect to knee flexion). In the present embodiment, the braking unit 16 is a rotary hydraulic braking unit and includes: a housing member 34 having a chamber where hydraulic oil flows in and out; and a switching valve 36. The rotation axis of the braking unit 16 coincides with the knee shaft 24. A braking state in which a braking force is generated against the rotation of the lower leg part 14 around the knee shaft 24 and a non-braking state in which the braking force is released are switched by the action of the switching valve 36. The switching valve 36 is controlled according to what part of the foot part 32 the load of the prosthetic leg wearer is applied. As the switching valve 36, either a normally open type or a normally closed type can be used. A normally open type is used here. As a rotary hydraulic braking device and the switching valve, those that are publicly known can be used. For example, the one described in the above-stated Patent Document 2 can be used.

The four-bar link mechanism 18 connects the thigh connection part 12 and the braking unit 16. The four-bar link mechanism 18 becomes deformed depending on the relative position between the thigh connection part 12 and the lower leg part 14. The four-bar link mechanism 18 allows for a relatively small rotation between the thigh connection part 12 and the braking unit 16 and further has the instant center S between the toe 32a and the heel 32b of the foot part 32. The term "small rotation" refers to a rotation with a very small rotation angle of, for example, 5° to 6° or less and is an expression used in contrast with a large rotation of 150° to 160° around the knee shaft 24. The small rotation can be a rotation of 2° to 3° or less, 6° to 9° or less, 10° to 20° or less, or 20° to 30° or less. A smaller angle is better in order not to cause the prosthetic leg wearer to feel anxiety or discomfort, while a larger angle is better in order to obtain a large displacement. In any case, the small rotation is desirably set so as not to cause the prosthetic leg wearer to feel anxiety or discomfort. The four-bar link mechanism 18 has a mechanical configuration and has an instant center S outside the components of the configuration. In the prosthetic leg knee joint 10 according to the present embodiment, what part of the foot part 32 the load of the prosthetic leg wearer is applied, that is, which one of the heel 32b and the toe 32a of the foot 32 the load is applied is detected using the instant center S located in a predetermined area outside the four-bar link mechanism 18 as a sensing point. Therefore, regardless of the posture of the prosthetic leg wearer, the correct detection can always be performed not only when walking on a flat ground but also when going down stairs or downhill. Based on the detection, the braking unit 16 can be controlled appropriately, and a flexible knee braking function can be obtained. In the present embodiment, the four-bar link mechanism 18 can be considered to be functioning as a detection unit that detects the relative position between the instant center S and the lower leg part.

In the present embodiment, the four-bar link mechanism 18 consists of an upper link part 39 provided in the thigh connection part 12, a lower link part 41 provided in the housing member 34 of the braking unit 16, and a plurality of connection link parts that connect the upper link part 39 and the lower link part 41. The connection link parts include a front link part 40 connecting a part of the upper link part 39 and a part of the lower link part 41 and a rear link part 42 connecting another part of the upper link part 39 and another part of the lower link part 41. The front end of the lower link part 41 and the lower end of the front link part 40 are connected by a shaft A, and the front end of the upper link part 39 and the upper end of the front link part 40 are connected by a shaft B. Further, the rear end of the upper link part 39 and the upper end of the rear link part 42 are connected by a shaft C, and the rear end of the lower link part 41 and the lower end of the rear link part 42 are connected by a shaft D. Thus, the four-bar link mechanism 18 according to the present embodiment has rotation axes at the four points: the shafts A, B, C, and D.

The portion of the front link part 40 above the shaft A serves as an actuator for the switching valve 36, and the braking unit 16 is activated when the relative position between the instant center S and the lower leg part 14 is in a predetermined state due to the deformation of the four-bar link mechanism 18 (more specifically, due to a small rotational movement around the shaft A of the front link part 40).

In the prosthetic leg knee joint 10 according to the present embodiment, the length of the upper link part 39 and the length of the lower link part 41 are different. The length of a link part is the distance between shafts that connect the link part and another link part. That is, the length of the upper link part 39 is the distance between the shaft B and the shaft C, and the length of the lower link part 41 is the distance between the shaft A and the shaft D. In this way, by making the length of the upper link part 39 and the length of the lower link part 41 different from each other, a straight line connecting the shaft A and the shaft B of the front link part 40 (hereinafter referred to as a straight line AB) and a straight line connecting the shaft C and the shaft D of the rear link part 42 (hereinafter referred to as a straight line CD) can be easily crossed at one point within a finite distance L from the knee shaft 24. This point serves as the instant center S for a small rotational movement of the upper link part 39 with respect to the lower link part 41. The finite distance L from the knee shaft 24 is preferably set so that the instant center S is located between the vicinity of the sole of the foot part 32 and the vicinity of the hip joint of the prosthetic leg wearer. In this case, since a more stable heel contact load and a toe off load can be distinguished from each other, a stable braking force can be exhibited regardless of the intention of the prosthetic leg wearer.

If the length of the upper link part 39 and the length of the lower link part 41 are the same, the straight line AB and the straight line CD become more parallel to each other as compared with the case where the lengths are set to be different from each other. Thus, it becomes difficult to set the instant center S within the finite distance L from the knee shaft 24. In this case, as the distance of the instant center approaches an infinite distance outside the range of the finite distance L, it becomes more difficult to obtain a stable knee braking function since a braking action force (switching valve pressing force or brake pressing force) of a certain degree or more cannot be obtained.

In the prosthetic leg knee joint 10 according to the present embodiment, the length of the lower link part 41 is shorter than the length of the upper link part 39. By making the length of the lower link part 41 shorter than the length of the upper link part 39, the instant center S, which is the intersection of the straight line AB and the straight line CD, can be easily positioned below the knee shaft 24. In this case, the instant center S is preferably placed between the toe 32*a* and the heel 32*b* of the foot part 32 as shown in FIG. 1, and in this case, the heel contact load and the toe off load can be clearly distinguished from each other. In other words, when the weight is applied to the heel 32*b* side of the foot part 32, the load line (floor reaction force) is located behind the instant center S, and the switching valve 36 is thus closed due to the deformation of the four-bar link mechanism 18, causing the prosthetic leg knee joint 100 to be in a state where the brake is being applied by the braking unit 16. On the other hand, when the weight is applied to the toe 32*a* side, the load line is located in front of the instant center S. Thus, different from the former case, the switching valve 36 becomes open due to the deformation of the four-bar link mechanism 18, causing the brake on the prosthetic leg knee joint 10 applied by the braking unit 16 to be released.

Figure 2:
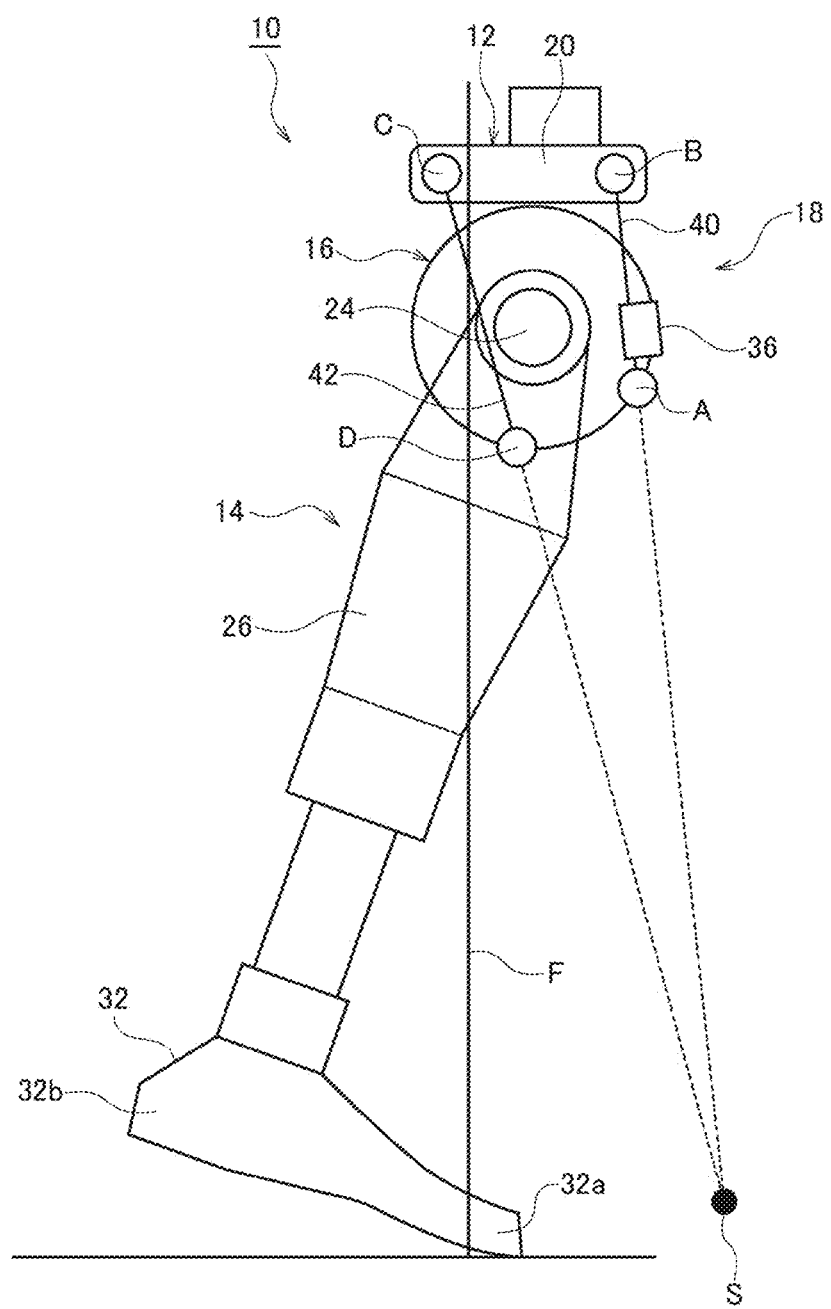
FIG. 2 is a diagram for explaining the action when toe strike occurs while the knee is flexed in the prosthetic leg knee joint according to the embodiment of the present invention.

FIG. 2 is a diagram for explaining the action when toe strike occurs while the knee is flexed in the prosthetic leg knee joint 10 according to the present embodiment. As described above, the knee shaft 24 coincides with the rotation axis of the braking unit 16, and the lower leg part 14 below the knee shaft 24 rotates largely during knee flexion. In the prosthetic leg knee joint 10, the braking unit 16 is connected to the thigh connection part 12 side by the four-bar link mechanism 18 such that the braking unit 16 hardly moves during knee flexion and the instant center S roughly stays at the original position (the position shown in FIG. 1). In this state, as shown in FIG. 2, when the toe 32*a* is grounded and the weight is applied, a load line F roughly represented by a line connecting the toe strike point and the hip joint is generated, and the load line F passes behind the knee shaft 24. Therefore, the prosthetic leg tends to move in the direction where the knee flexion angle increases. However, in the prosthetic leg knee joint 10 according to the present embodiment, since the load line F at the time of the toe strike is located behind the instant center S, which is the sensing point, the switching valve 36 is closed due to the deformation of the four-bar link mechanism 18. Since the braking force is generated by the braking unit 16, an increase in the flexion angle, that is, the knee bending can be prevented. Further, when the position of the instant center S is appropriately selected, the distance between the toe strike point and the instant center S increases as the flexion angle increases, and the braking force can thus be generated more reliably.

Figure 3:
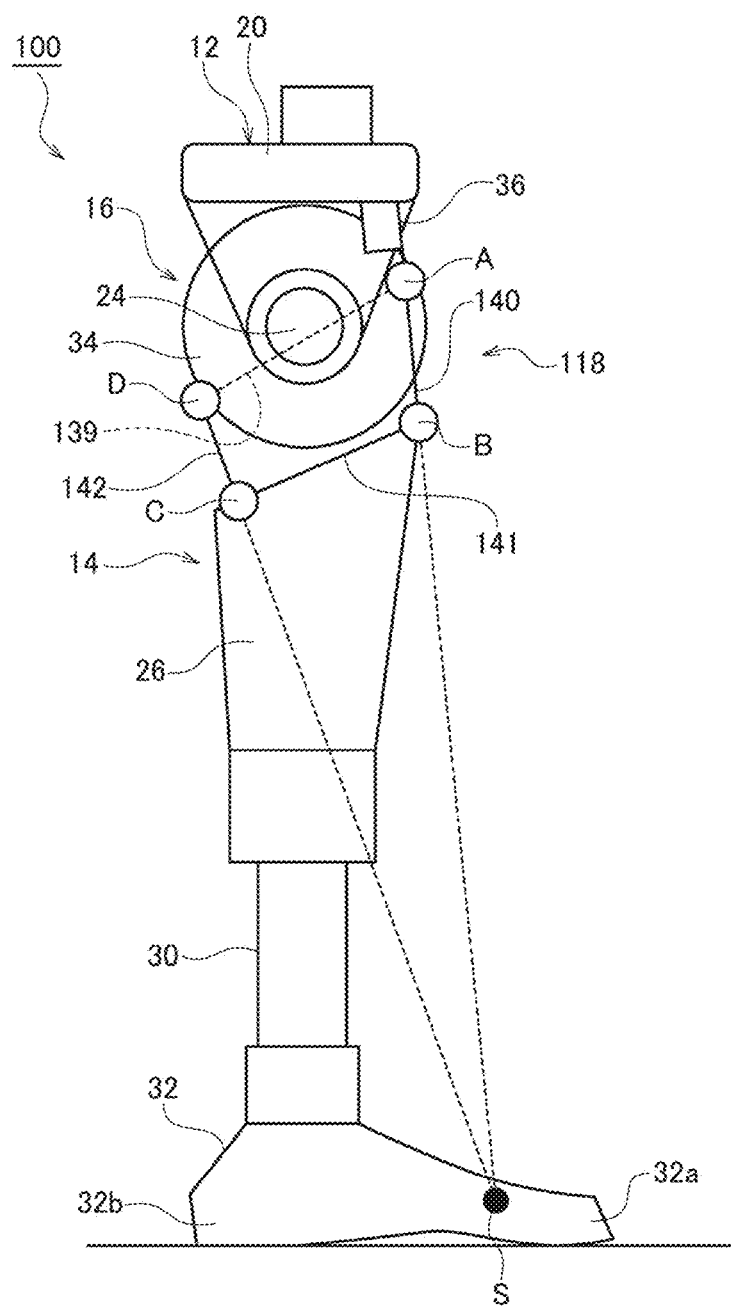
FIG. 3 is a diagram for explaining a prosthetic leg knee joint according to a comparative example.

A comparative example will be described now in order to clarify the configuration and operation of the prosthetic leg knee joint 10 according to the present embodiment. FIG. 3 is a diagram for explaining a prosthetic leg knee joint 100 according to the comparative example. The prosthetic leg knee joint 100 according to the comparative example corresponds to the prosthetic leg described in Patent Document 2 described above.

The prosthetic leg knee joint 100 according to the comparative example is different from the prosthetic leg knee joint 10 according to the present embodiment in that a four-bar link mechanism 118 connects a lower leg part 14 and a braking unit 16. In other words, in the prosthetic leg knee joint 100 according to the comparative example, when an upper link part 139 is provided on a housing member 34 of the braking unit 16 and a lower link part 141 is provided on a frame 26 of the lower leg part 14, the upper link part 139 and the lower link part 141 are connected via a front link part 140 and a rear link part 142. The front end of the upper link part 139 and the upper end of the front link part 40 are connected by a shaft A, and the front end of the lower link part 141 and the lower end of the front link part 140 are connected by a shaft B. Further, the rear end of the lower link part 141 and the lower end of the rear link part 142 are connected by a shaft C, and the rear end of the upper link part 139 and the upper end of the rear link part 142 are connected by a shaft D. As described, the four-bar link mechanism 118 according to the comparative example also has rotation axes at the four points: the shafts A, B, C, and D.

Further, in the prosthetic leg knee joint 100 according to the comparative example, the portion of the front link part 140 above the shaft A serves as an actuator for the switching valve 36, and the braking unit 16 is activated due to the deformation of the four-bar link mechanism 118. The instant center S of a small rotational movement of the upper link part 139 relative to the lower link part 141 is at the intersection of a straight line connecting the shaft A and the shaft B of the front link part 140 and a straight line connecting the shaft C and the shaft D of the rear link part 142. This instant center S is used as a sensing point and is placed between the toe 32*a* and the heel 32*b* of the foot part 32. When the weight is applied to the heel 32*b* side of the foot part 32, the load line (floor reaction force) is located behind the instant center S, and the switching valve 36 is thus closed due to the deformation of the four-bar link mechanism 18, causing the prosthetic leg knee joint 100 to be in a state where the brake is being applied by the braking unit 16. On the other hand, when the weight is applied to the toe 32*a* side, the load line is located in front of the instant center S. Thus, different from the former case, the switching valve 36 becomes open due to the deformation of the four-bar link mechanism 118, causing the brake on the prosthetic leg knee joint 100 applied by the braking unit 16 to be released.

Figure 4:
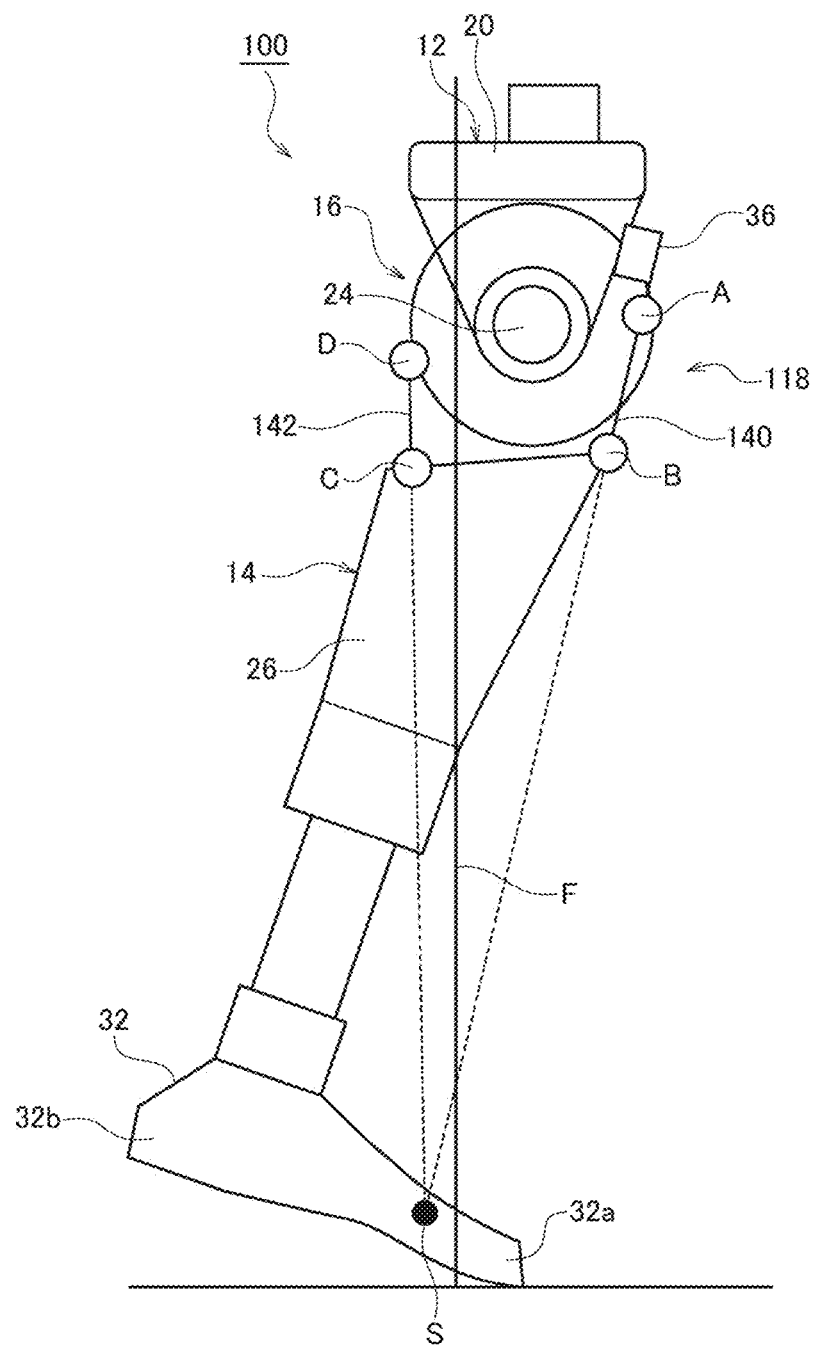
FIG. 4 is a diagram for explaining the action when toe strike occurs while the knee is flexed in the prosthetic leg knee joint according to the comparative example.

FIG. 4 is a diagram for explaining the action when toe strike occurs while the knee is flexed in the prosthetic leg knee joint 100 according to the comparative example. In the prosthetic leg knee joint 100 according to the comparative example, the braking unit 16 is connected to the lower leg part 14 side by the four-bar link mechanism 118. Therefore, the braking unit 16 also rotates at the same time during the knee flexion. Therefore, unlike the prosthetic leg knee joint 10 according to the present embodiment, the instant center S at the time of knee flexion moves backward from the original position (the position shown in FIG. 3) as shown in FIG. 4. In this state, as shown in FIG. 4, when the toe 32a is grounded and the weight is applied, a load line F is generated, and the load line F passes behind the knee shaft 24. Therefore, the prosthetic leg tends to move in the direction where the knee flexion angle increases. In this case, in the prosthetic leg knee joint 100 according to the comparative example, since the instant center S has moved greatly backward along with knee flexion, the load line F is located in front of the instant center S. As a result, the switching valve 36 becomes open. Thus, there is a possibility that the braking force by the braking unit 16 is not generated and the flexion angle is increased, that is, the knee bending occurs.

Based on the comparison with the prosthetic leg knee joint 100, according to the prosthetic leg knee joint 10 relating to the present embodiment, the relative position between the instant center S and the thigh connection part 12 is substantially constant within a finite distance L from the knee shaft, regardless of the relative position between the thigh connection part 12 and the lower leg part 14. Thus, the braking unit 16 can be operated without fail even when toe strike occurs while the knee is flexed, and it can be found that high stance stability can be obtained. It should be noted that although the instant center S slightly shifts as the four-bar linkage 18 is deformed, the relative position between the instant center S and the thigh connection part is also considered to be substantially constant even in this case.

Figure 5A:
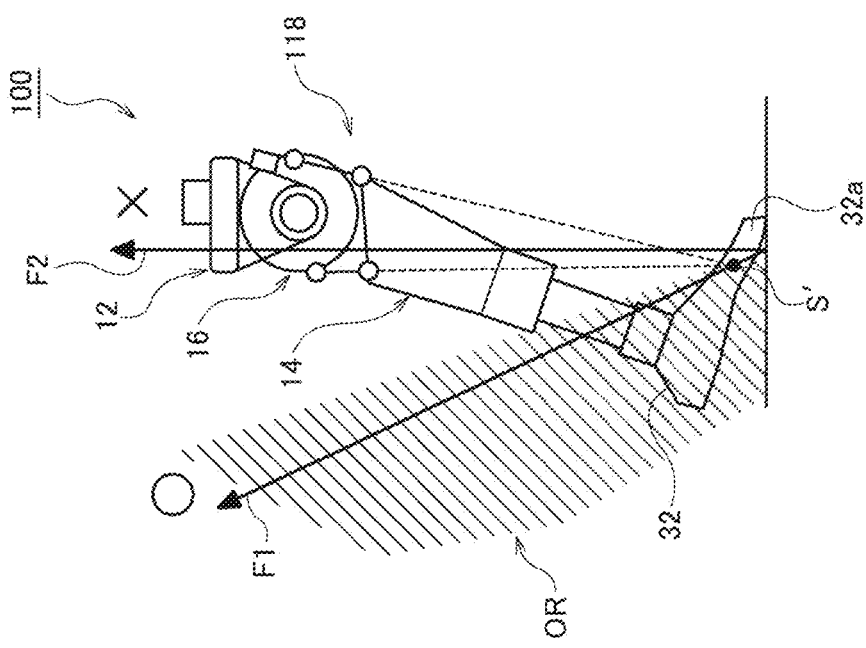
FIG. 5A and FIG. 5B are diagrams comparing the stable operating range of a braking portion when toe strike occurs while the knee is flexed.
Figure 5B:
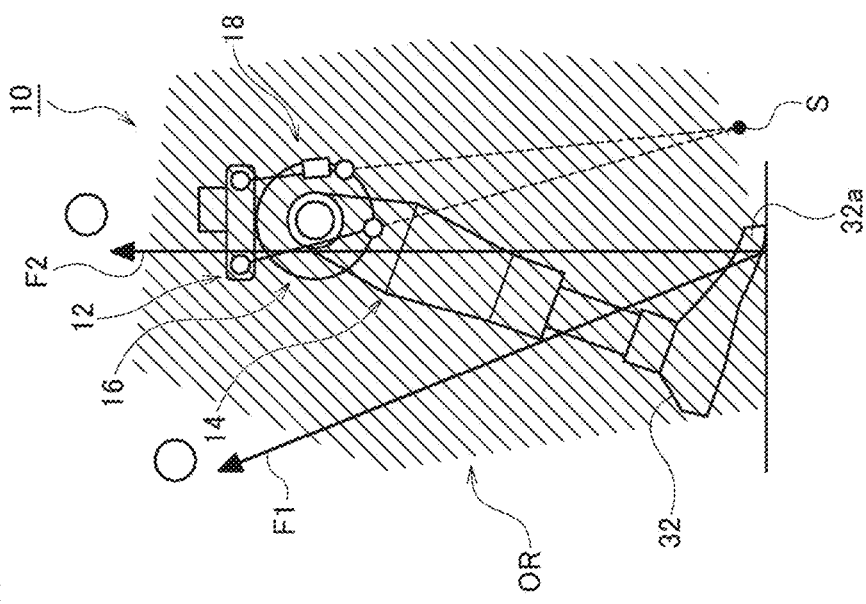

FIG. 5A and FIG. 5B are diagrams comparing the stable operating range of a braking unit 16 when toe strike occurs while the knee is flexed. FIG. 5A shows a stable operating range OR of the braking unit 16 in the prosthetic leg knee joint 10 according to the present embodiment. FIG. 5B shows a stable operating range OR of the braking unit 16 in the prosthetic leg knee joint 100 according to the comparative example. When the load line passing through the toe 32a of the foot part 32 is located within the stable operating range OR, the braking unit 16 exhibits a braking force, and when the load line is outside the stable operating range OR, the braking unit 16 does not exhibit a braking force.

In the prosthetic leg knee joint 100 according to the comparative example shown in FIG. 5B, the braking unit 16 is connected to the lower leg part 14 side by the four-bar link mechanism 118. Therefore, the instant center S at the time of knee flexion moves backward as compared to that at the time of knee extension. Therefore, as shown in FIG. 5B, the stable operating range OR of the braking unit 16 is reduced as compared with that at the time of knee extension. Therefore, when a load is applied backward from the toe 32a (load line F1), a braking force is generated by the braking unit 16, and knee bending can thus be prevented. However, when a load is applied in a vertical direction from the toe 32a (load line F2), the braking force by the braking unit 16 is not generated, and knee bending may occur.

On the other hand, in the prosthetic leg knee joint 10 according to the present embodiment shown in FIG. 5A, since the braking unit 16 is connected to the thigh connection part 12 side by the four-node link mechanism 18, the instant center S (sensing point) hardly moves even during knee flexion and is located in front of the toe 32a of the foot part 32. Therefore, as shown in FIG. 5A, almost the entire area around the prosthetic leg knee joint 10 is in the stable operating range OR of the braking unit 16 as in the case of knee extension. Therefore, even when a load is applied backward from the toe 32a (load line F1) or a load is applied in the vertical direction from the toe 32a (load line F2), the braking force by the braking unit 16 is generated, and knee bending can thus be prevented.

In the above-described embodiment, the four-bar link mechanism 18 is formed using the components of the prosthetic leg. For example, a part of the thigh connection part 12 is used as the upper link part 39 and a part of the housing member 34 of the braking unit 16 is used as the lower link part 41. However, the four-bar link mechanism may be formed using a member used only for forming the link mechanism (the member is referred to as a link-dedicated member) without using the components of the prosthetic leg. When the four-bar link mechanism is formed using the components of the prosthetic leg as in the present embodiment, it is not necessary to separately arrange a link-dedicated member, and the structure can therefore be made compact.

Figure 6:
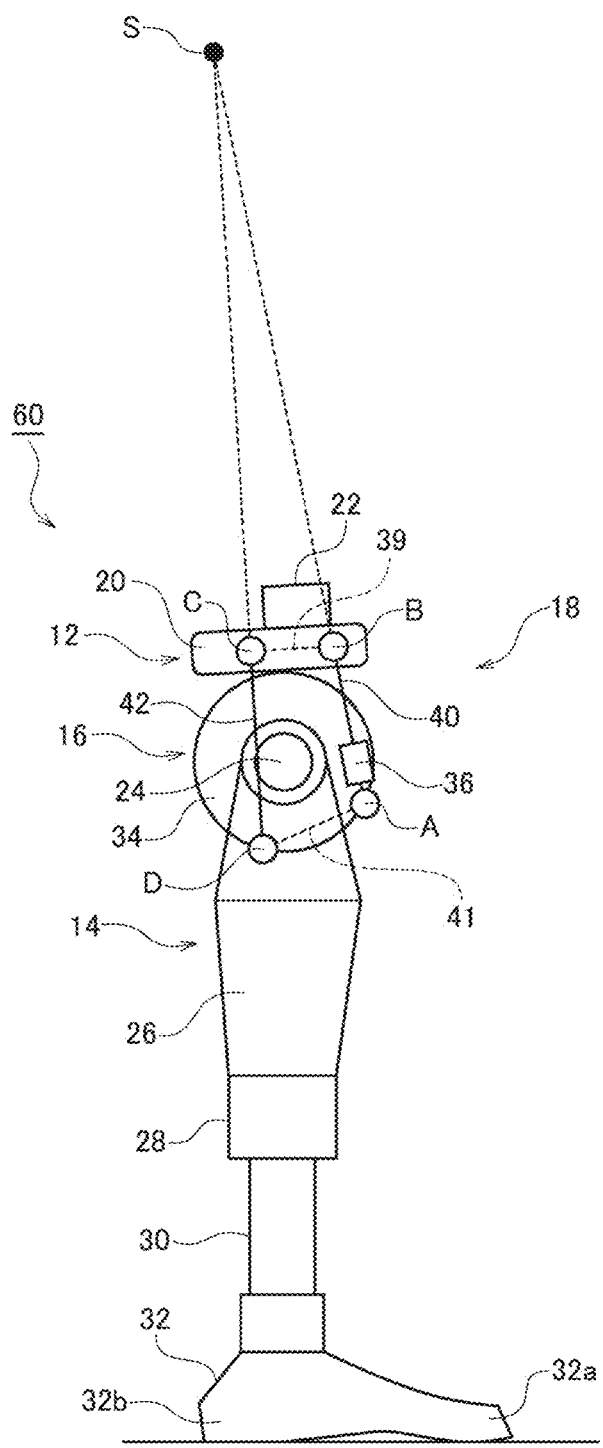
FIG. 6 is a diagram for explaining a prosthetic leg knee joint according to another embodiment of the present invention.

FIG. 6 is a diagram for explaining a prosthetic leg knee joint 60 according to another embodiment of the present invention. The prosthetic leg knee joint 60 shown in FIG. 6 also includes a four-bar link mechanism 18 as a reference position setting unit. The four-bar link mechanism 18 connects the thigh connection part 12 and the braking unit 16. The four-bar link mechanism 18 is deformed due to the relative position between the thigh connection part 12 and the lower leg part 14, and the braking unit 16 is activated when the relative position between the instant center S and the lower leg part 14 is in a predetermined state due to the deformation.

The prosthetic leg knee joint 60 according to the present embodiment is different from the above-described prosthetic leg knee joint 10 in that the length of the lower link part 41 is longer than the length of the upper link part 39. By making the length of the lower link part 41 longer than the length of the upper link part 39, the instant center S, which is the intersection of the straight line AB and the straight line CD, can be easily positioned above the knee shaft 24.

Figure 7:
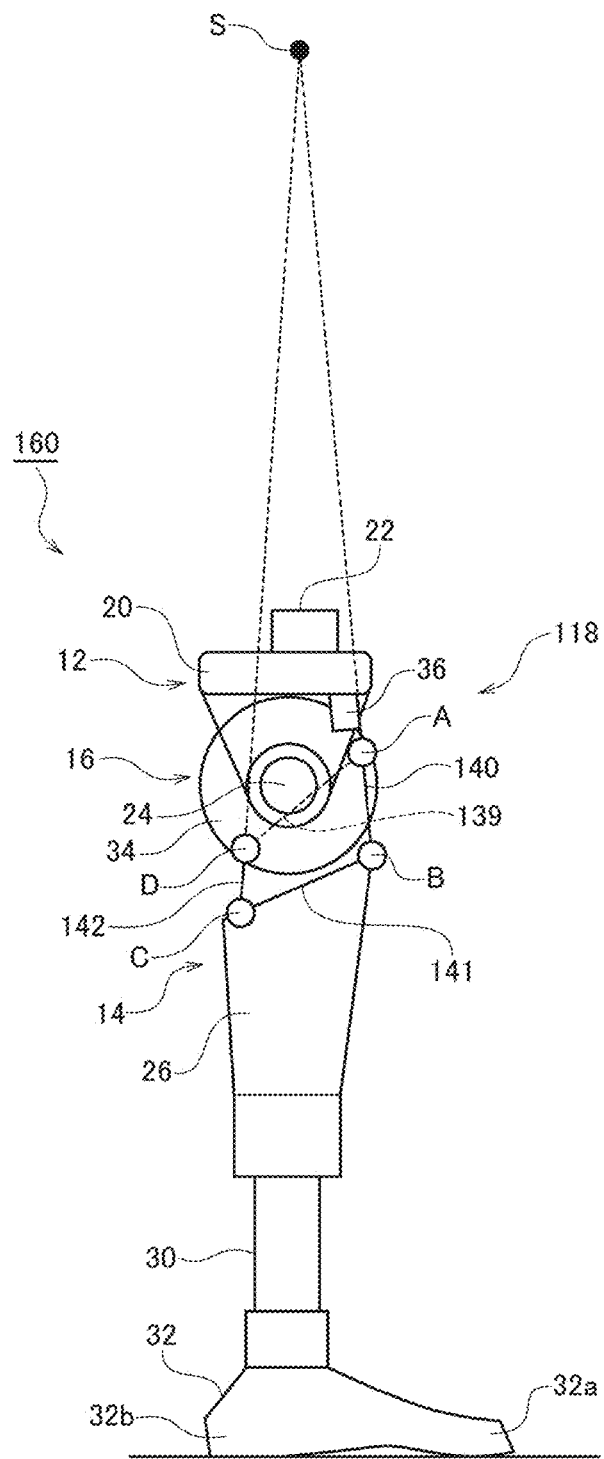
FIG. 7 is a diagram for explaining a prosthetic leg knee joint according to a comparative example.

FIG. 7 is a diagram for explaining a prosthetic leg knee joint 160 according to a comparative example. The prosthetic leg knee joint 160 according to this comparative example is different from the prosthetic leg knee joint 60 shown in FIG. 6 in that a four-bar link mechanism 118 connects a lower leg part 14 and a braking unit 16. Also in the prosthetic leg knee joint 160, the length of the lower link part 141 is longer than the length of the upper link part 139. As a result, the instant center S, which is the intersection of the straight line AB and the straight line CD, is located above the knee shaft 24.

Figure 8A:
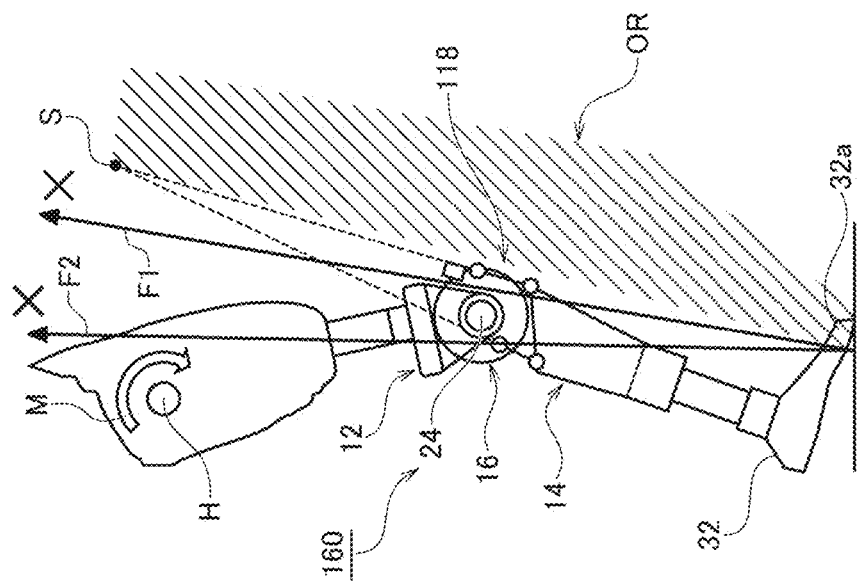
FIG. 8A and FIG. 8B are diagrams comparing the stable operating range of a braking portion when toe strike occurs while the knee is bent.
Figure 8B:
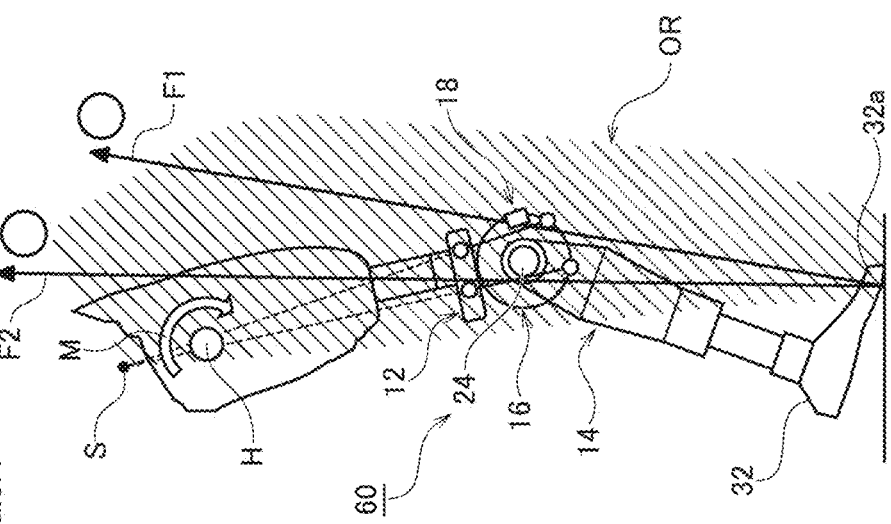

FIG. 8A and FIG. 8B are diagrams comparing the stable operating range of a braking unit 16 when toe strike occurs while the knee is flexed. FIG. 8A shows a stable operating range OR of the braking unit 16 in the prosthetic leg knee joint 60 according to the present embodiment. FIG. 8B shows a stable operating range OR of the braking unit 16 in the prosthetic leg knee joint 160 according to the comparative example. When the load line passing through the toe 32a of the foot part 32 is located within the stable operating range OR, the braking unit 16 exhibits a braking force, and when the load line is outside the stable operating range OR, the braking unit 16 does not exhibit a braking force. When the instant center S is located above the knee shaft 24, there is a stable operating range in front of a line connecting the toe strike point and the instant center S.

In the prosthetic leg knee joint 160 according to the comparative example shown in FIG. 8B, the braking unit 16 is connected to the lower leg part 14 side by the four-bar link mechanism 118. Therefore, the instant center S at the time of knee flexion moves forward as compared to that at the time of knee extension shown in FIG. 7. Therefore, as shown in FIG. 8B, the stable operating area OR at the time of knee flexion is located far ahead of the knee shaft 24. Therefore, when a load is applied slightly in front of the knee shaft 24 from the toe 32a (load line F1), or when a load is applied in the vertical direction from the toe 32a (load line F2), a braking force by the braking unit 16 is not generated, and knee bending may occur.

On the other hand, in the prosthetic leg knee joint 60 according to the present embodiment shown in FIG. 8A, since the braking unit 16 is connected to the thigh connection part 12 side by the four-node link mechanism 18, the instant center S hardly moves even during knee flexion. Therefore, as shown in FIG. 8A, the stable operating range OR does not move forward like the prosthetic leg knee joint 160 according to the comparative example, and the periphery of the knee shaft is included in the stable operating range OR. Therefore, even when a load is applied slightly in front of the knee shaft 24 from the toe 32a (load line F1) or a load is applied in the vertical direction from the toe 32a (load line F2), the braking force by the braking unit 16 is generated, and knee bending can thus be prevented.

As in the prosthetic leg knee joint 10 shown in FIG. 1, by making the length of the lower link part 41 shorter than the length of the upper link part 39, the instant center S can be positioned below the knee shaft 24. On the other hand, as in the prosthetic leg knee joint 60 shown in FIG. 6, by making the length of the lower link part 41 longer than the length of the upper link part 39, the instant center S can be positioned above the knee shaft 24. Whether the instant center S is positioned above or below the knee axis 24 is preferably set in accordance with the prosthetic leg wearer knee joint.

There are some prosthetic leg wearers who have high activity ability and want to control the action of the braking force according to their intention. In general, those who have high activity ability have strong muscle strength that remains at the amputated part of the hip joint. Such prosthetic leg wearers with high activity ability have a tendency of not liking a braking force working regardless of their intention. In the case of such prosthetic leg wearers with high activity ability, the instant center S is preferably set above the knee shaft 24. As described above, when the instant center S is located above the knee shaft 24, there is a stable operating range in front of a line connecting the toe strike point and the instant center S (see FIG. 8A). When a prosthetic leg wearer puts the hip joint extensor to work, the load line tilts forward (so as to balance the moment M at a hip joint H) and enters the stable operating range OR (see the load line F1). When the prosthetic leg wearer intends to bend the knee, the wearer weakens the strength of the hip joint extensor and, in some cases, bends the hip joint H. Thereby, since the load line enters an unstable range (outside the stable operating range OR), the braking force by the braking unit 16 can be released. As described, for prosthetic leg wearers with high activity ability, the instant center S located above the knee shaft 24 is preferred in terms of living various lifestyles including sports and recreation since the generation of the braking force can be intentionally selected. As described above, in the prosthetic leg knee joint 160 according to the comparative example, since the instant center S moves forward during knee flexion, the stable operating range OR is located far ahead of the knee shaft 24 (see FIG. 8B). Therefore, controlling the load line in the stable operating range OR requires an excessive hip joint extension moment, which is practically impossible.

On the other hand, users undergoing rehabilitation during the early stage following amputation, the elderly, and the like have weak hip joint muscle strength, and it is difficult to perform such control as described above. Therefore, in the case of such a prosthetic leg wearer, a wide stable operating range OR is preferably set while having the instant center S located below the knee shaft 24 so as to exert a stable braking force regardless of the intention of the prosthetic leg wearer.

When a link-dedicated member is arranged, it is possible to form a link mechanism using both the member and a component of the prosthetic leg. In this case, it is possible to set the instant center below the knee shaft by making the length of the lower link part shorter than the length of the upper link part for the link mechanism using the component of the prosthetic leg and to set the instant center above the knee shaft by making the length of the lower link part longer than the length of the upper link part for the link mechanism using the link-dedicated member.

Figure 9:
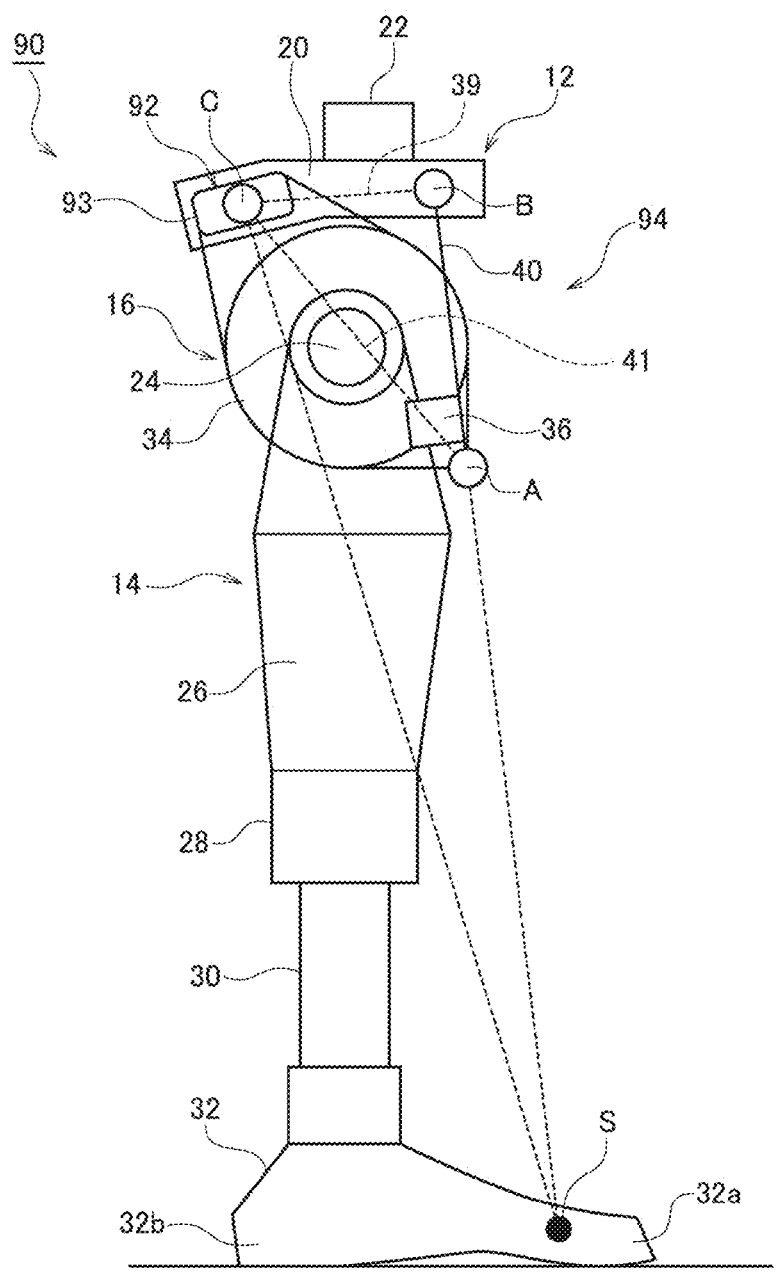
FIG. 9 is a diagram for explaining a prosthetic leg knee joint according to still another embodiment of the present invention.

FIG. 9 is a diagram for explaining a prosthetic leg knee joint 90 according to still another embodiment of the present invention. The prosthetic leg knee joint 90 shown in FIG. 9 is different from the above-described prosthetic leg knee joint 10 in that a link mechanism 94 using a sliding element 92 is provided as a reference position setting unit. The link mechanism 94 connects the thigh connection part 12 and the braking unit 16. When the relative position between the instant center S and the lower leg part 14 is in a predetermined state due to the deformation of the link mechanism 94 caused according to the relative position between the thigh connection part 12 and the lower leg part 14, the movement of the lower leg part 14 is braked by the braking unit 16.

The link mechanism 94 includes an upper link part 39 provided in the thigh connection part 12, a lower link part 41 provided in the braking unit 16, a front link part 40 serving as a connection link part that connects a part of the upper link part 39 and a part of the lower link part 41, and a sliding element 92 connecting another part of the upper link part 39 and another part of the lower link part 41. In the present embodiment, the sliding element 92 is a slide bearing in which a shaft C can slide in a predetermined direction inside a housing 93 provided at the rear end of the thigh connection part 12. The front end of the lower link part 41 and the lower end of the front link part 40 are connected by a shaft A, and the front end of the upper link part 39 and the upper end of the front link part 40 are connected by a shaft B. Further, the rear end of the upper link part 39 and the rear end of the lower link part 41 are connected by the shaft C of the sliding element 92.

The portion of the front link part 40 above the shaft A serves as an actuator for the switching valve 36, and the braking unit 16 is activated when the relative position between the instant center S and the lower leg part 14 is in a predetermined state due to the deformation of the link mechanism 94. The instant center S of the link mechanism 94 is at the intersection of a straight line (straight line AB) connecting the shafts A and B of the front link part 40 and a straight line passing through the shaft C of the sliding element 92 and perpendicular to the sliding direction, and is set within a finite distance L from the knee shaft 24. In the present embodiment, the instant center S is placed between the toe 32a and the heel 32b of the foot part 32 as shown in FIG. 9. Also in the present embodiment, the instant center S serves as a sensing point so as to detect what part of the foot part 32 the load of the prosthetic leg wearer is applied, that is, which one of the heel 32b and the toe 32a of the foot part 32 the load is applied and control the braking unit 16 based on the detection result. Also in the present embodiment, the link mechanism 94 can be considered to be functioning as a detection unit that detects the relative position between the instant center S and the lower leg part.

Also in the prosthetic leg knee joint 90 relating to the present embodiment, the relative position between the instant center S and the thigh connection part 12 is substantially constant within a finite distance L from the knee shaft 24 regardless of the relative position between the thigh connection part 12 and the lower leg part 14. Thus, the braking unit 16 can be operated without fail even when toe strike occurs while the knee is flexed, and high stance stability can be obtained.

Figure 10:
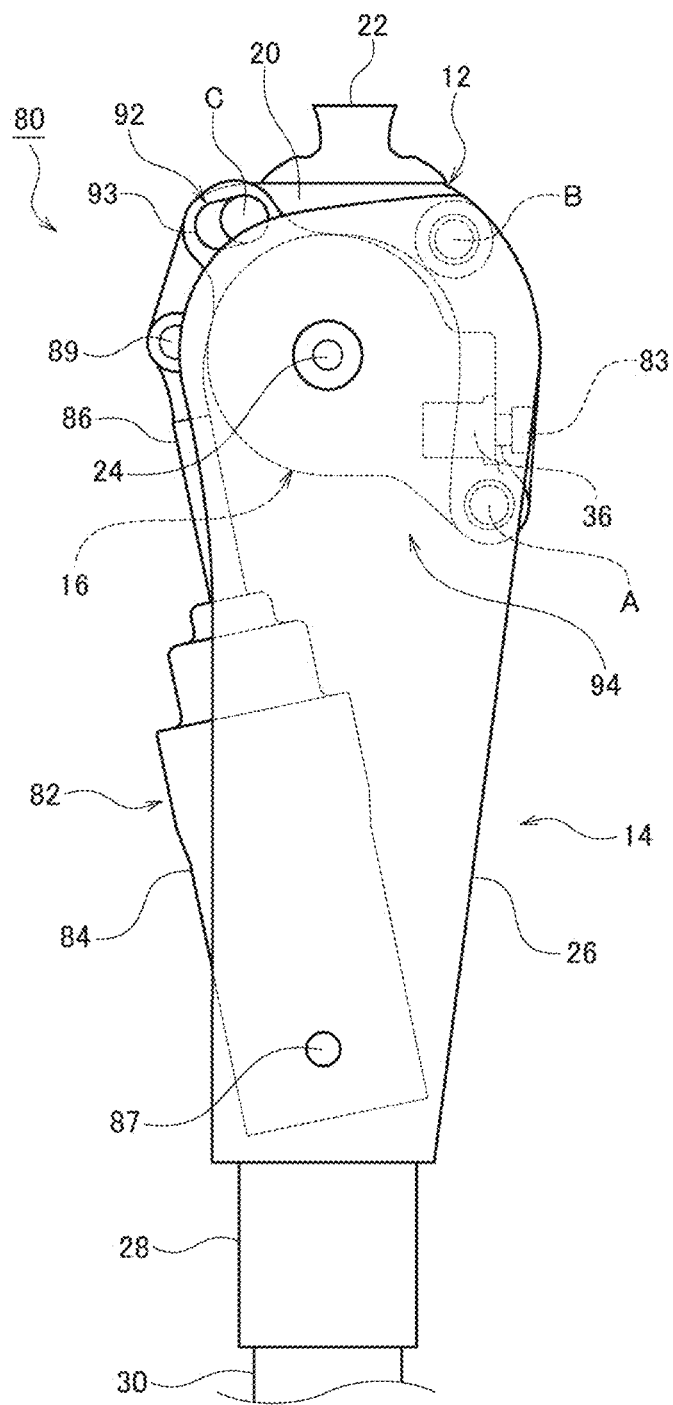
FIG. 10 is a lateral view showing an exemplary embodiment of a prosthetic leg knee joint provided with a link mechanism that uses a sliding element.
Figure 11:
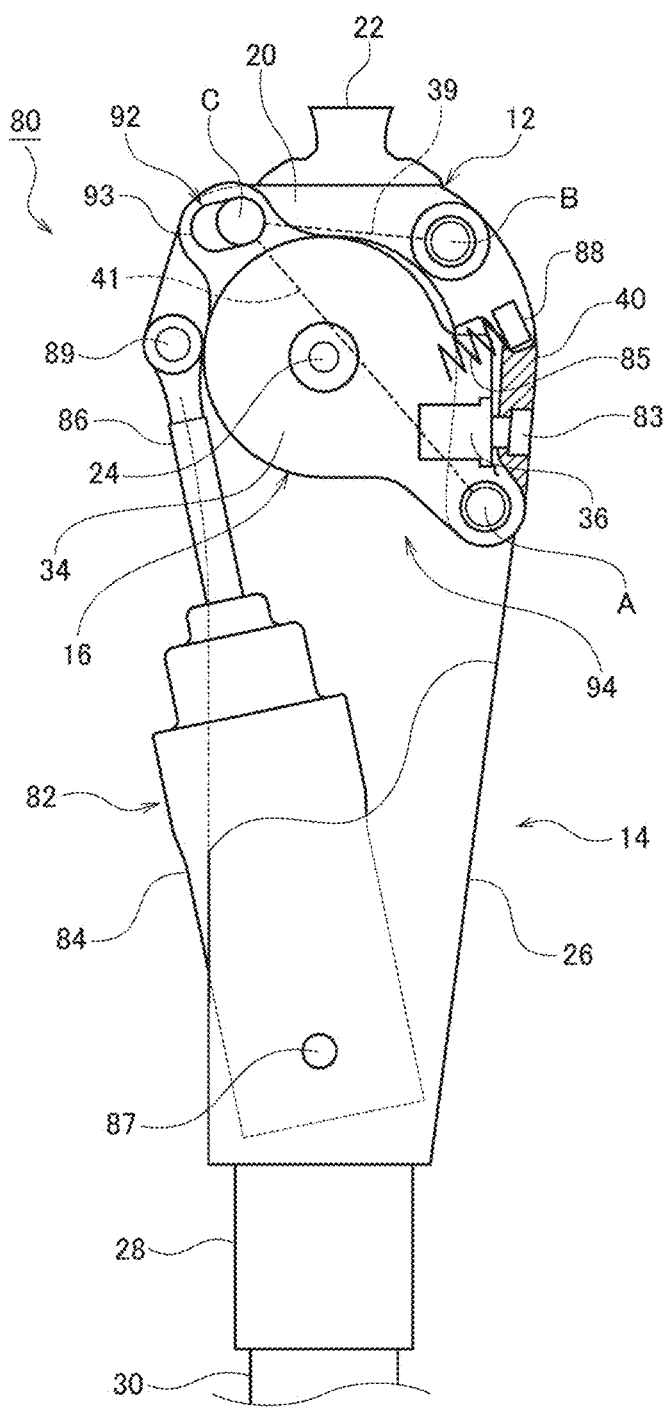
FIG. 11 is a cross-sectional schematic diagram showing the prosthetic leg knee joint provided with a link mechanism that uses a sliding element.

FIG. 10 is a lateral view showing an exemplary embodiment of a prosthetic leg knee joint. FIG. 11 is a schematic cross-sectional view showing an exemplary embodiment of a prosthetic leg knee joint.

In the same way as in the prosthetic leg knee joint 90 shown in FIG. 9, a prosthetic leg knee joint 80 shown in FIG. 10 and FIG. 11 is a prosthetic leg knee joint including a link mechanism 94 using a sliding element 92 as a reference position setting unit.

As shown in FIG. 10 and FIG. 11, the prosthetic leg knee joint 80 includes a cylinder device 82 as an auxiliary drive unit that assists the movement of the knee according to the knee flexion angle. The cylinder device 82 may be an air cylinder or an oil hydraulic cylinder. The cylinder device 82 includes a cylinder tube 84 and a piston rod 86 that is movable relative to the cylinder tube 84. The cylinder device 82 is provided so as to connect a knee plate 20 and a lower leg part 14. More specifically, the cylinder tube 84 is rotatably supported by a lower shaft 87 provided in the lower leg part 14, and the piston rod 86 is rotatably supported by an upper shaft 89 provided in the knee plate 20. By controlling the cylinder device 82 according to the knee flexion angle around the knee shaft 24 detected by a sensor (not shown), for example, the lower leg part 14 is swung in accordance with the swinging of the foot at the time of leg swing, and comfortable walking of the prosthetic leg wearer can be realized.

In the prosthetic leg knee joint 80 according to the exemplary embodiment, the braking unit 16 is a rotary hydraulic braking device and includes: a housing member 34 having a chamber where hydraulic oil flows in and out; and a switching valve 36. The rotation axis of the braking unit 16 coincides with the knee shaft 24. A braking state in which a braking force is generated against the rotation of the lower leg part 14 around the knee shaft 24 and a non-braking state in which the braking force is released are switched by the action of the switching valve 36. The switching valve 36 is controlled according to what part of the foot part the load of the prosthetic leg wearer is applied.

As shown in FIG. 11, the braking unit 16 is provided with a return spring 85 and an adjustment plug 88. The return spring 85 is a spring for opening the switching valve 36 in a non-load state (normal state). The adjustment plug 88 is for adjusting the initial deflection amount of the return spring 85.

The link mechanism 94 includes an upper link part 39 provided in the knee plate 20, a lower link part 41 provided in the braking unit 16, a front link part 40 connecting a part of the upper link part 39 and a part of the lower link part 41, and a sliding element 92 connecting another part of the upper link part 39 and another part of the lower link part 41. In the present exemplary embodiment, the sliding element 92 is a slide bearing in which the shaft C can slide in a predetermined direction inside a housing 93 provided at the rear end of the knee plate 20. The front end of the lower link part 41 and the lower end of the front link part 40 are connected by a shaft A, and the front end of the upper link part 39 and the upper end of the front link part 40 are connected by a shaft B. Further, the rear end of the upper link part 39 and the rear end of the lower link part 41 are connected by the shaft C of the sliding element 92.

The portion of the front link part 40 above the shaft A serves as an actuator 83 for the switching valve 36, and the braking unit 16 is activated when the relative position between the instant center S and the lower leg part 14 is in a predetermined state due to deformation of the link mechanism 94 of a predetermined degree or more. As explained in FIG. 9, the intersection of a straight line connecting the shafts A and B of the front link part 40 and a straight line passing through the shaft C of the sliding element 92 and perpendicular to the sliding direction serves as the instant center of the link mechanism 94 and is set within a finite distance from the knee shaft 24. The instant center is placed between the toes of the foot part and the heel. This instant center serves as a sensing point so as to differentiate a case where the load of the prosthetic leg wearer is applied to the heel of the foot part from a case where the load is applied to the toes and control the braking unit 16 based on the detection result.

Figure 12A:
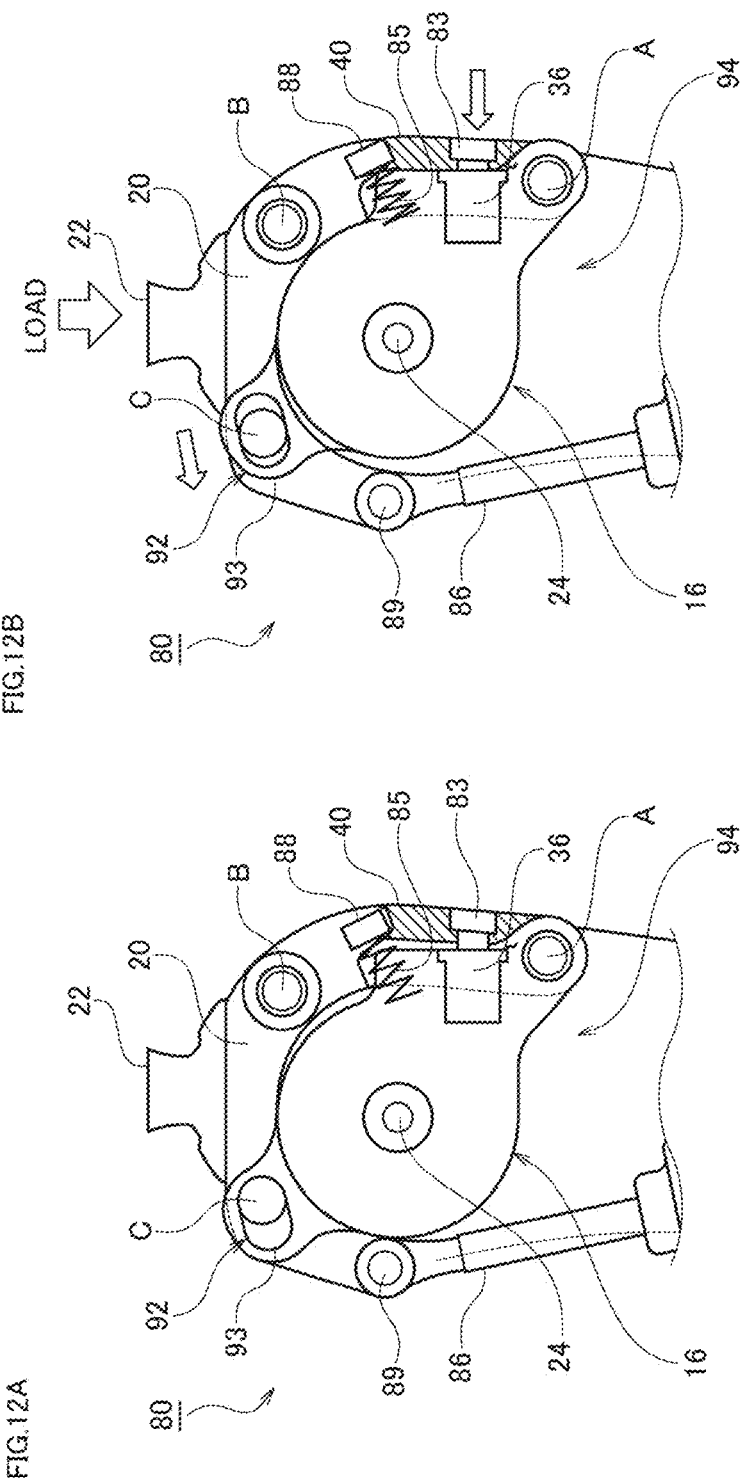
FIG. 12A and FIG. 12B are diagrams for explaining the operation of the prosthetic leg knee joint according to an exemplary embodiment.
Figure 12B:
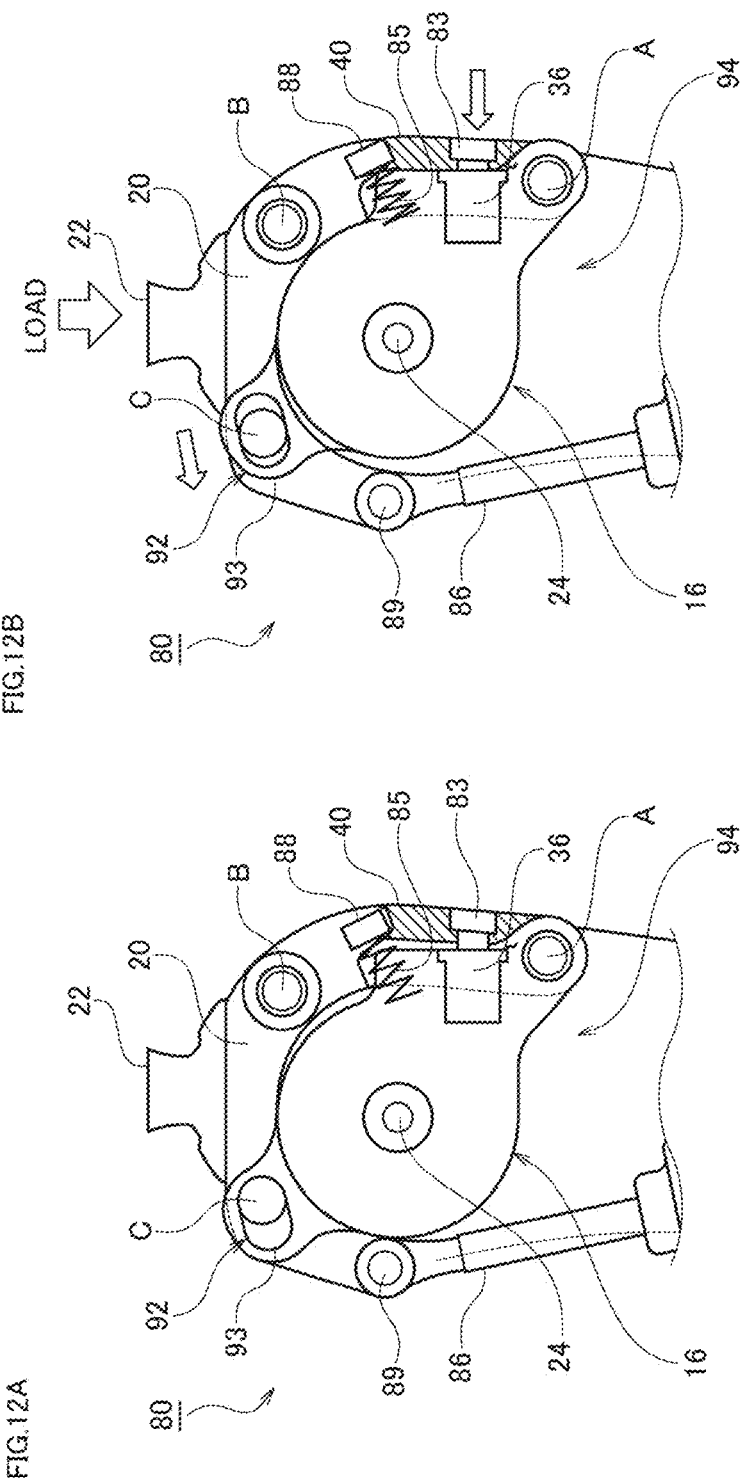

FIG. 12A and FIG. 12B are diagrams for explaining the operation of a prosthetic leg knee joint 90 according to an exemplary embodiment. FIG. 12A shows a prosthetic leg knee joint 80 in a non-load state (normal state), and FIG. 12B shows the prosthetic leg knee joint 80 in a load state.

As shown in FIG. 12A, the shaft C of the sliding element 92 is located at one end inside the housing 93 in a non-load state. In this state, the switching valve 36 is open due to the force of the return spring 85, and no braking force is generated by the braking unit 16. On the other hand, in the load state, as shown in FIG. 12B, the shaft C of the sliding element 92 slides toward the other end inside the housing 93. By the sliding of the shaft C, the link mechanism 94 is deformed, and by this deformation, the switching valve 36 becomes closed via the actuator 83 provided in the front link part 40, and the braking force by the braking unit 16 is generated. At this time, the return spring 85 is being compressed. When the load is released, the force of the compressed return spring 85 acts such that the link mechanism 94 returns to the normal state, and as a result, the switching valve 36 becomes open. By rotating the adjustment plug 88 so as to adjust the initial deflection amount of the return spring 85, the sensitivity of a series of operations of the braking unit 16 described above can be adjusted.

Described above is an explanation of the present invention based on the embodiments. The embodiments are intended to be illustrative only and it will be understood by those skilled in the art that various modifications to constituting elements and processes could be developed and that such modifications are also within the scope of the present invention.

For example, in the above-described embodiments, a rotary hydraulic braking circuit using hydraulic resistance is adopted as the braking unit. However, the form of the braking unit is not limited to the hydraulic type. For example, those using frictional resistance (drum type, band type, disk type, spring type) may be used or those that drive a mechanical stopper (cam type, link type, clutch) may be used.

In the above-described embodiment, a single-shaft prosthetic leg knee joint with a single knee shaft has been described. However, the present invention can be also applied to a multi-shaft prosthetic leg knee joint in which the knee shaft is formed of a plurality of shafts. That is, the braking unit needs to be arranged such that the rotation axis of the braking unit coincides with one of the plurality of shafts of the multi-shaft knee joint, and a small rotational movement of the front link part or the rear link part needs to be applied to the braking unit.

In the above-described embodiment, a single braking unit is arranged. Alternatively, a plurality of braking units may be arranged.

In the above-described embodiments, a four-bar link mechanism is employed as a multi-bar link mechanism that connects the thigh connection part and the braking unit. However, the link mechanism is not limited to a four-bar link mechanism, and a multi-bar link mechanism having a plurality of link parts including at least an upper link part and a lower link part can be employed.

In the above-described embodiments, a braking unit is operated using a small rotational movement of a front link part. Alternatively, a braking unit may be operated using a small rotational movement of a rear link part.

What is claimed is:

1. A prosthetic leg comprising:
   a thigh connection part;
   a lower leg part that is provided rotatably around the thigh connection part;
   a multi-bar link mechanism that is deformed in accordance with a relative position between the thigh connection part and the lower leg part; and
   a braking unit that brakes a movement of the lower leg part when the multi-bar link mechanism is deformed to a predetermined degree or more, wherein
   the multi-bar link mechanism is configured to set an instant center, a relative position of the instant center with respect to the thigh connection part being constant regardless of the relative position between the thigh connection part and the lower leg part, and
   the braking unit is configured to brake the movement of the lower leg part in accordance with the relative position between the instant center set by the multi-bar link mechanism and the lower leg part.

2. The prosthetic leg according to claim 1, wherein the multi-bar link mechanism consists of an upper link part provided in the thigh connection part, a lower link part provided in the braking unit, and a plurality of connection link parts that connect the upper link part and the lower link part.

3. The prosthetic leg according to claim 2, wherein a length of the upper link part and the length of the lower link part are different.

4. The prosthetic leg according to claim 3, wherein the length of the lower link part is shorter than the length of the upper link part.

5. The prosthetic leg according to claim 4, wherein the instant center is set between a vicinity of a sole and a vicinity of a hip joint of a prosthetic leg wearer.

6. The prosthetic leg according to claim 3, wherein the length of the lower link part is longer than the length of the upper link part.

7. The prosthetic leg according to claim 2, wherein the connection link parts include:
   a front link part connecting a part of the upper link part and a part of the lower link part; and
   a rear link part connecting another part of the upper link part and another part of the lower link part.

8. The prosthetic leg according to claim 1, wherein the multi-bar link mechanism includes an upper link part provided in the thigh connection part, a lower link part provided in the braking unit, a connection link part connecting a part of the upper link part and a part of the lower link part, and a sliding element connecting another part of the upper link part and another part of the lower link part.

* * * * *